United States Patent [19]
Hunter et al.

[11] Patent Number: 5,342,769
[45] Date of Patent: Aug. 30, 1994

[54] MICROBIAL DEHALOGENATION USING METHANOSARCINA

[75] Inventors: Robert M. Hunter; Frank M. Stewart, both of Bozeman, Mont.

[73] Assignee: Yellowstone Environmental Science, Inc., Bozeman, Mont.

[21] Appl. No.: 940,439

[22] Filed: Sep. 4, 1992

[51] Int. Cl.$^5$ .................. C12P 5/02; C12P 1/04; C02F 3/30

[52] U.S. Cl. .................. 435/166; 435/167; 435/170; 435/262.5; 210/601; 210/605; 210/610

[58] Field of Search .................. 435/167, 166, 262.5, 435/170; 210/601, 605, 610

[56] References Cited

U.S. PATENT DOCUMENTS

| | | | |
|---|---|---|---|
| 4,022,665 | 5/1977 | Ghosh et al. | 195/27 |
| 4,877,736 | 10/1989 | Fliermans | 435/183 |
| 4,959,315 | 9/1990 | Nelson et al. | 435/167 |
| 5,024,949 | 6/1991 | Hegeman et al. | 435/262 |
| 5,076,927 | 12/1991 | Hunter | 210/603 |

OTHER PUBLICATIONS

Fathepure et al., *Appl. Environ. Microbiology* 54 (12) 1988, pp. 2976–2980.

*Primary Examiner*—Douglas W. Robinson
*Assistant Examiner*—L. Blaine Lankford

[57] ABSTRACT

A method for bioremediation of hazardous wastes is disclosed. The method can be used for anaerobic treatment of a liquid or slurry hazardous waste stream (e.g., industrial wastewater or sludge) or for treatment of contaminated groundwater. Removal of halogenated (e.g., chlorinated) hydrocarbons, such as tetrachloroethylene, trichloroethylene, 1,1,1-trichloroethane and similar xenobiotics is possible. The method involves biotransformation of (dehalogenation) halogenated hydrocarbons by means of natural methanogenic bacteria, *Methanosarcina barkeri* strain 227 and/or *Methanosarcina vacuolata*. These methanogens can accomplish cometabolism of chlorinated hydrocarbons during metabolism of a primary substrate such as hydrogen-carbon dioxide, methanol, methylamine, dimethylamine, trimethylamine and acetate. Reductive dechlorination, energy conservation and control of air pollution are accomplished.

4 Claims, 3 Drawing Sheets

MICROBIAL DEHALOGENATION USING METHANOSARCINA

This invention was made with Government support under Contract No. DAAH01-922-C-R068 awarded by the Defense Advanced Research Projects Agency, a component of the U.S. Department of Defense. The Government has certain rights in the invention. It is described in detail in a report entitled "Biomimetric Process for Hazardous Waste Remediation" by Yellowstone Environmental Science, Inc., 320 S. Willson Ave., Bozeman, Mont., USA 59715.

TECHNICAL FIELD

This invention relates to a method for microbial dehalogenation of halogenated compounds and, more particularly, to a method for dechlorinating chlorinated hydrocarbon hazardous wastes by means of cometabolism by methanogenic bacteria of the species *Methanosarcina barkeri* and/or *Methanosarcina vacuolata*.

BACKGROUND

The activities of the U.S. Department of Defense (DoD) and its contractors result in the generation of large amounts of hazardous wastes. Many of the constituents of concern are waterborne or have become waterborne as a result of leaks or spills. Among the most troublesome of these wastes are organic solvents. Even at low concentrations, these constituents are often toxic, tend to be resistant to conventional treatment methods and are persistent in the environment. Common halogenated hydrocarbon waste constituents include the following:

tetrachloroethylene (PCE)
trichloroethylene (TCE)
1,1,1-trichloroethane (TCA)

Halogenated hydrocarbons are used as solvents and in vapor degreasing operations.

Prior art processes have been developed that accomplish microbial dehalogenation of halogenated hydrocarbons. Processes for dechlorination of chlorinated aliphatic hydrocarbons by aerobic microorganisms are disclosed in U.S. Pat. Nos. 4,877,736, 4,959,315, and 5,024,949, the disclosures of which patents are incorporated by reference herein as if fully set forth.

Because of the significant advantages of accomplishing dehalogenation under anaerobic conditions, many researchers have investigated methods involving anaerobic reductive dehalogenation. Reductive dehalogenation is an oxidation-reduction reaction that results in the replacement of a halogen atom with a hydrogen atom. See Egli, Tschan, Scholtz, Cook and Leisinger in Applied and Environmental Microbiology, Vol. 54, pp. 2819-2824 (1988); Fathepure, Tiedje and Boyd in Applied and Environmental Microbiology, Vol. 54, pp. 327-330 (1988) and Freedman and Gossett in Applied and Environmental Microbiology, Vol. 55, pp. 2144-2151 (1989).

Different methanogenic bacteria strains vary in their ability to reductively dechlorinate chlorinated aliphatic hydrocarbons. *Methanosarcina mazei* strain S6 and Methanosarcina sp. strain DCM isolated from a methanogenic enrichment growing on chlorophenol can produce TCE from PCE while *Methanosarcina acetivorans* and a highly enriched culture of Methanothrix sp. also obtained from the chlorophenol enrichment do not have this ability. See Fathepure and Boyd in Applied and Environmental Microbiology, Vol. 54, pp. 2976-2980 (1988); Fathepure and Boyd in FEMS Microbiology Letters, Vol. 49, pp. 149-156 (1988) and Fathepure, Nengu and Boyd in Applied and Environmental Microbiology, Vol. 53, pp. 267114 2674 (1987). *Methanobacterium thermoautotrophicum* can produce ethylene (ethene) from 1,2-dichloroethylene (1,2-dichloroethene). See Egli, Scholtz, Cook and Leisinger in FEMS Microbiology Letters, Vol. 43, pp. 257-261 (1987). *Methanobacterium thermoautotrophicum* can also dechlorinate carbon tetrachloride (tetrachloromethane). See Egli, Stromeyer, Cook and Leisinger in FEMS Microbiology Letters, Vol. 68, pp. 207-212 (1990). *Methanobacterium thermoautotrophicum* strain AH, *Methanococcus deltae* strain ALH and *Methanococcus thermolithotrophicus* can produce ethane from bromoethane, ethylene from bromoethane sulfonate, 1,2-dibromoethane and 1,2-dichloroethane and acetylene from 1,2-dibromoethylene. See Belay and Daniels in Applied and Environmental Microbiology, Vol. 53, pp. 1604-1610 (1987).

Krone, Laufer, Thauer and Hogenkamp in Biochemistry, Vol. 28, pp. 10061-10065 (1989) disclosed that purified coenzyme $F_{430}$ obtained from *Methanobacterium thermoautotropicum* strain Marburg grown on $H_2$—$CO_2$ catalyzed the dechlorination of carbon tetrachloride ($CCl_4$) to form chloroform ($CHCl_3$) methylene chloride ($CH_2Cl_2$), methyl chloride ($CH_3Cl$), methane ($CH_4$) and small amounts of ethane ($CH_3CH_3$) with titanium (III) citrate as electron donor. Coenzyme $F_{430}$ also catalyzed the reduction of chloroform, methylene chloride and methyl chloride individually.

Concerning the dehalogenation ability of methanogens of the genus Methanosarcina, the prior art teaches that only three strains, namely *Methanosarcina mazei* strain S6, Methanosarcina sp. strain DCM, and *Methanosarcina barkeri* strain Fusaro have the ability to dehalogenate as whole cells. For example, Fathepure and Boyd in FEMS Microbiology Letters, Vol. 49, pp. 149-156 (1988) stated "The dechlorination of PCE by our Methanosarcina sp. appears to be a unique characteristic as other acetate-utilizing methanogens show either significantly lower or no activity against PCE." Acceptance of these teachings is illustrated by use of pure cultures of these Methanosarcina strains in research documenting their ability to dehalogenate carbon tetrachloride, chloroform and bromoform. See Mikesell and Boyd in Applied and Environmental Microbiology, Vol. 56, pp. 1198-1201 (1990). Methanosarcina sp. strain DCM has been shown not to be the same bacterium as *Methanosarcina barkeri* strain 227 (ATCC 43241). See Fathepure and Boyd in Applied and Environmental Microbiology, Vol. 54, pp. 2976-2980 (1988).

Jablonski and Ferry in FEMS Microbiology Letters, Vol. 96, pp. 55-60 (1992) disclosed that purified carbon monoxide dehydrogenase enzyme complex obtained from *Methanosarcina thermophila* dechlorinated TCE in the presence of either carbon monoxide or titanium (III) citrate as a reductant. About one-third of the TCE was transformed to cis 1,2-dichloroethylene (predominantly), trans 1,2-dichloroethylene, vinyl chloride, ethylene and (traces of) 1,1-dichloroethylene.

Krone, Laufer, Thauer and Hogenkamp in Biochemistry, Vol. 28, pp. 10061-10065 (1989) disclosed that cell suspensions of *Methanosarcina barkeri* strain Fusaro (ATCC 29787) harvested from a methanol or acetate medium could dehalogenate carbon tetrachloride to form chloroform, methylene chloride and minor amounts of methyl chloride with carbon monoxide as the electron donor. This strain was also able to dehalogenate chloroform and methylene chloride individually under the same conditions. The strain was unable to accomplish the dehalogenation of methyl chloride.

Krone and Thauer in FEMS Microbiology Letters, Vol. 90, pp. 201–204 (1992) disclosed that cell suspensions of *Methanosarcina barkeri* strain Fusaro (ATCC 29787) harvested from a methanol medium were able to catalyze the reductive dehalogenation of trichlorofluoromethane (CFC-11, also known as FREON 11) to form $CHFCl_2$, CO and fluoride and minute amounts of $CH_2FCl$ in the presence of either $H_2$ or CO. The presence of either $H_2$ or CO was necessary for dehalogenation of CFC-11 to occur. Dehalogenation of CFC-12 (dichlorodifluoromethane) occurred at less than 5 percent of the rate at which CFC-11 was dehalogenated. CFC-11 completely inhibited methanogenesis in *Methanosarcina barkeri* strain Fusaro at the concentrations tested (6.7 μmol in a 120-ml serum bottle containing 10 ml of cell suspension).

In summary, the prior art teaches that some species of the genus Methanosarcina (e.g., *Methanosarcina acetivorans*) are unable to dehalogenate halogenated hydrocarbons such as PCE. It also teaches that, in the genus Methanosarcina, only Methanosarcina sp. strain DCM, *Methanosarcina mazei* strain S6 and *Methanosarcina barkeri* strain Fusaro possess dehalogenation ability as whole cells. The prior art teaches that the ability for a bacterial strain to catalyze a dehalogenation reaction varies not only with the halogenated hydrocarbon (electron acceptor) but also with the presence or absence of a specific reducing agent (electron donor). No prior art teaches or suggests that *Methanosarcina barkeri* strain 227 (ATCC 43241) or that any strain of *Methanosarcina vacuolata* can dechlorinate any halogen. No prior art teaches or suggests that any methanogen can dechlorinate TCA during heterotrophic growth.

Methanogenic bacteria are archaeobacteria that belong to one of the orders Methanobacteriales, Methanococcales, or Methanomicrobiales. The family Methanosarcinacae is one of two families in the order Methanobacteriales. The family Methanosarcinacae includes three genera: *Methanosarcina, Methanolobus* and *Methanothrix*.

*Methanosarcina barkeri* is a species of the genus Methanosarcina. Its energy-yielding metabolism involves methane production. During autotrophic metabolism, $H_2$—$CO_2$, and during heterotrophic metabolism, methanol, (mono)methylamine, dimethylamine, trimethylamine and acetate are reduced to $CH_4$ without intermediate oxidation to $CO_2$. Growth and $CH_4$ formation are more rapid in media with $H_2$—$CO_2$ or methanol as substrates than with acetate Cells of *Methanosarcina barkeri* do not contain gas vesicles. Optimum growth is obtained at pH 7.0 and at 30°–40° C.

Four strains of the methanogen *Methanosarcina barkeri* are available from the American Type Culture Collection (ATCC), 12301 Parklawn Drive, Rockville, Md. 20852-1776. Their strain names and accession numbers from the ATCC and the Deutsche Sammulung yon Mikroorganismen (DSM), Gottingen, Federal Republic of Germany are as follows:

| Strain name | Accession number | |
|---|---|---|
| | ATCC | DSM |
| 3 | 29786 | 805 |
| Fusaro | 29787 | 804 |
| DM | 29894 | — |
| FA"9 | 43240 | — |
| 227 | 43241 | 1538 |

Information on these strains and their growth requirements is available in the literature. See Hippe, Caspari, Fiebig and Gottschalk in Proceedings of the National Academy of Science USA, Vol. 76, pp. 494–498 (1979); Mah, Smith and Baresi in Applied and Environmental Microbiology, Vol. 35, pp. 1174–1184 (1978); Smith and Lequerica in Journal of Bacteriology, Vol. 164, pp. 618–625 (1985); Scherer and Sahm in European Journal of Applied Microbiology and Biotechnology, Vol. 12, pp. 28–35 (1981); Kandler and Hippe in Archives of Microbiology, Vol. 113, pp. 57–60 (1977) and Staley, Bryant, Pfennig and Holt (eds.) in Bergey's Manual of Systematic Bacteriology, Vol. 3, Baltimore: Williams & Wilkins (1989).

*Methanosarcina vacuolata* is also a species of the genus Methanosarcina. $H_2$—$CO_2$, methanol, methylamines and acetate may be used as substrates. Growth on methanol is faster than on acetate. The cells of *Methanosarcina vacuolata* may contain gas vesicles. Optimum growth is obtained at pH 7.5 and 37°–40° C.

One strain of the methanogen *Methanosarcina vacuolata* is available from the ATCC. The strain name and accession numbers from the ATCC and the DSM are as follows:

| Strain name | Accession number | |
|---|---|---|
| | ATCC | DSM |
| Z-761 | 35090 | 1232 |

Information on this strain is available in the literature. See Zhilina and Zavarzin in Mikrobiologiya, Vol. 48, pp. 279–285 (1979); Zhilina and Zavarzin in International Journal of Systematic Bacteriology, Vol. 37, pp. 281–283 (1987) and Staley, Bryant, Pfennig and Holt (eds.) in Bergey's Manual of Systematic Bacteriology, Vol. 3, Baltimore: Williams & Wilkins (1989).

NATURE OF THE INVENTION

The present invention provides a method for microbial dehalogenation. A halogen is any of the nonmetallic elements fluorine, chlorine, iodine, bromine and astatine. Dehalogenation is removal of a halogen from an organic compound. The invention is a useful, novel and unobvious new use for certain methanogenic bacteria (methanogens).

The present method may be practiced in situ in the pore space of underground formations or it may be practiced in batch or continuous culture in conventional reactors. Essentially axenic (pure) cultures of selected methanogens may be used or mixed cultures which include the selected methanogens may be used.

If essentially axenic (95+ percent pure) cultures are used, pure cultures may be obtained from a culture collection, such as the American Type Culture Collection (ATCC), 12301 Parklawn Drive, Rockville, Md. 20852-1776. If enrichment from mixed cultures is used, enrichment can be accomplished in a variety of ways, including using "kinetic control" of continuous cultures as an "open system" selection mechanism. With kinetic control, growth rate (dilution rate or mean cell residence time) is used to favor particular microorganisms and disfavor others. In general, it involves operation of serial continuous cultures at successively lower dilution rates. If cell recycle is practiced, the downstream reactor(s) are operated at a greater mean cell residence time (MCRT) than upstream reactor(s). This enrichment technique can be used to enrich in an upstream reactor microorganisms or consortia that are capable of more rapid growth than those enriched in a downstream reactor. The enrichment technique of kinetic control is disclosed in U.S. Pat. Nos. 4,022,665 and 5,076,927, the disclosures of which patents are incorporated herein by references as if fully set forth.

In addition to kinetic control, the invention may use other factors to impose selection pressures on mixed cultures that continuously inoculate open systems. A second fundamental factor is the oxidation-reduction potential (ORP) of the culture medium. In this regard, three different conditions may be used: aerobic, anoxic and anaerobic. Under aerobic conditions, dissolved molecular oxygen ($O_2$) is present. Under anoxic conditions, $O_2$ is substantially absent. Under anaerobic conditions, a substantially negative (e.g., $-200$ millivolts) oxidation reduction potential (ORP) exists in the medium.

A third factor that is used as an enrichment means is the availability of a limiting substrate. A limiting substrate is one that is available in a growth-limiting amount relative to other medium components. In the absence of easily degraded substrates, the availability of a xenobiotic limiting substrate effectively selects for microorganisms capable of its metabolism. In the instance of cometabolism, the primary substrate (the substrate fueling growth, be it electron donor or electron acceptor) is used as the limiting substrate.

A fourth factor imposing selection pressure is medium temperature. In general, three temperature ranges may be used: room temperature $=20°-25°$ C., mesophilic temperature $=30°-40°$ C. and thermophilic temperature $=50°-60°$ C.

In a preferred embodiment, hazardous waste comprising at least one halogenated hydrocarbon is transferred to a reactor, wherein the process of microbial dehalogenation is accomplished. An anaerobic environment is maintained in the reactor. The contents of the reactor may or may not be completely mixed by recirculation or other means. Certain methanogenic bacteria (which produce methane biologically) are grown in either suspended continuous culture or on biofilms or in both ways. The biofilms may be in a fixed-film reactor, such as a packed bed reactor. Alternatively, if contaminated groundwater is being treated, methanogenesis may occur, at least in part, in biofilms that colonize the pore space of a porous underground formation after the reactor effluent is reinjected into the ground. The reactor is operated at substantially constant ($\pm 2°$ C.) temperature and at a substantially constant ($\pm 0.2$ units) pH.

In a preferred embodiment, the reactor is operated as a completely mixed continuous stirred tank reactor (CSTR) with or without cell recycle at a predetermined dilution rate or mean cell residence time that enriches in the reactor a mixed culture that includes methanogenic bacteria. Reductive dehalogenation (e.g., dechlorination or debromination) of at least a portion of the remaining halogenated hydrocarbons also occurs. Methane gas is separated from the liquid effluent of the reactor.

Methane is a saturated hydrocarbon and an alkane. During methane synthesis by methanogenic bacteria, reductive dehalogenation of halogenated hydrocarbons occurs. One end product of reductive dechlorination of such chlorinated hydrocarbons as PCE and TCE may be ethylene. Ethylene is an unsaturated hydrocarbon and an alkene.

In some embodiments, the methane gas is used as fuel in internal combustion engines used to drive process-related pumps and generate waste heat or is burned to generate waste heat. Waste heat is used to heat the reactors and their contents.

A second preferred embodiment of the method involves operation of at least two reactors in series as disclosed in U.S. Pat. No. 5,076,927 to accomplish first sulfate reduction and then methanogenesis. Dehalogenation and methanogenesis are accomplished, in part, by methanogenic bacteria of the species *Methanosarcina barkeri* and/or *Methanosarcina vacuolata*. Details of the methods incorporated in U.S. Pat. No. 5,076,927 are presented in Robert M. Hunter's 1989 Montana State University doctoral thesis entitled "Biocatalyzed Partial Demineralization of Acidic Metal Sulfate Solutions", which thesis is available from University Microfilms International, 300 North Zeeb Road, Ann Arbor, Mich. 48106-1346 as Order No. 9019886.

A third preferred embodiment of the method involves operation of a denitrification reactor in series with a methanogenic reactor. Dehalogenation and methanogenesis are accomplished, in part, by methanogenic bacteria of the species *Methanosarcina barkeri* and/or *Methanosarcina vacuolata*.

In an alternative embodiment, the liquid effluent from the methanogenic reactor is transferred to another reactor, wherein an aerobic process step is accomplished. An aerobic environment is maintained in the reactor by introducing molecular oxygen or air to the reactor contents. The contents of the reactor may or may not be completely mixed. Aerobic microorganisms are grown in either suspended continuous culture or on biofilms. Mineralization of remaining organic waste constituents occurs and the effluent from the process may be released to the environment.

It is an object of the invention to provide a process for treatment of hazardous waste streams. Another object of the invention is to conserve energy in that anaerobic processes do not require (energy intensive) aeration. Methanogenic bacteria produce biogas that can be used to maintain appropriate reactor temperatures. Another object of the invention is to prevent air pollution in that loss of volatile hydrocarbons to the atmosphere (as often occurs with aerobic treatment processes) does not occur. The only gaseous products released to the environment are nitrogen and carbon dioxide, as methane ($CH_4$) and ethylene are oxidized during the use (e.g., combustion) of biogas. Another object of the invention is to minimize waste sludge production in that, compared to aerobic processes, very little biomass (waste sludge) is produced. It is another object of the invention that reductive dehalogenation of halogenated hydrocarbons occurs in at least one anaerobic process step. Further objects and advantages of the invention will become apparent from a consideration of the drawings and ensuing description of them.

BRIEF DESCRIPTION OF THE DRAWINGS

These features will be better understood by reference to the accompanying drawings that illustrate presently preferred embodiments of the invention.

In the drawings.

DETAILED DESCRIPTION OF THE INVENTION

Figure 1:
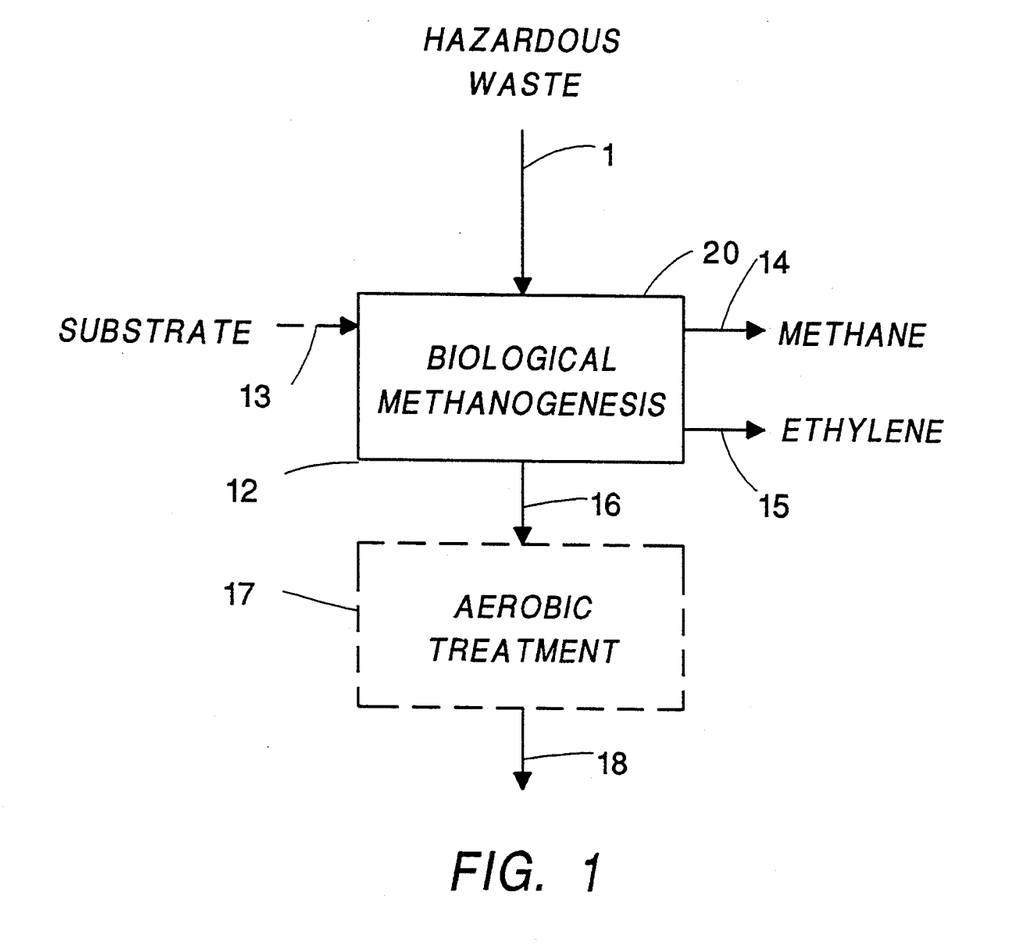
FIG. 1 is a schematic diagram of a first preferred embodiment of the invention.

Reference is now made to FIG. 1 which is a highly schematic block diagram illustrating a preferred embodiment of the invention, the dashed lines representing possible variations in the process. Hazardous waste 1 is the primary input to the process. Hazardous waste 1 includes at least one halogenated hydrocarbon. Examples of halogenated hydrocarbons include tetrachloroethylene (PCE), trichloroethylene (TCE), and 1,1,1-trichloroethane (TCA).

Hazardous waste 1 is delivered to reactor 12. In reactor 12, dehalogenation (e.g., dechlorination) and methanogenic reactions occur. Dehalogenation and methanogenesis are accomplished, in part, by methanogenic bacteria of the species *Methanosarcina barkeri* and/or *Methanosarcina vacuolata*. Dechlorination occurs under methanogenic conditions as a result of cometabolism of a primary substrate 13, which may be any substrate of methanogens of the genus Methanosarcina, e.g., $H_2$—$CO_2$, methanol, methylamines or acetate.

The end products of methanogenesis are methane 14 and carbon dioxide. The end product of dechlorination of PCE and TCE may be ethylene 15, a non-hazardous gas. If PCE or TCE is present in hazardous waste 1, reactor 12 contents are degassed to ensure that ethylene 15 does not reach high enough levels to inhibit methanogenesis. Methane formation by *Methanosarcina barkeri* is reversibly inhibited by 50 percent at a 3.6–7.2 $\mu M$ ethylene (ethene) concentration in the aqueous phase. When ethylene 15 is removed by purging with an inert gas such as nitrogen ($N_2$) or by imposing a vacuum on the headspace 20 of third reactor 12, no inhibition occurs. Ethylene can be oxidized by aerobic bacteria. Both methane and ethylene may be burned to produce heat for the process or otherwise used beneficially.

In an alternative embodiment, at least a portion of the methanogenic process step occurs underground. In this embodiment, at least a portion of reactor 12 is the pore space of an underground formation. Methanogenesis occurs in biofilms enriched in that environment.

If the methanogenic process is used to pretreat wastewater prior to discharge of liquid effluent 16 to a municipal wastewater system, it is likely that no additional treatment would be required. If liquid effluent 18 must contain very low levels of organics, then a subsequent aerobic treatment step is provided in reactor 17. This could be accomplished in a conventional aerobic treatment process, such as the activated sludge process or the trickling filter process.

Figure 2:
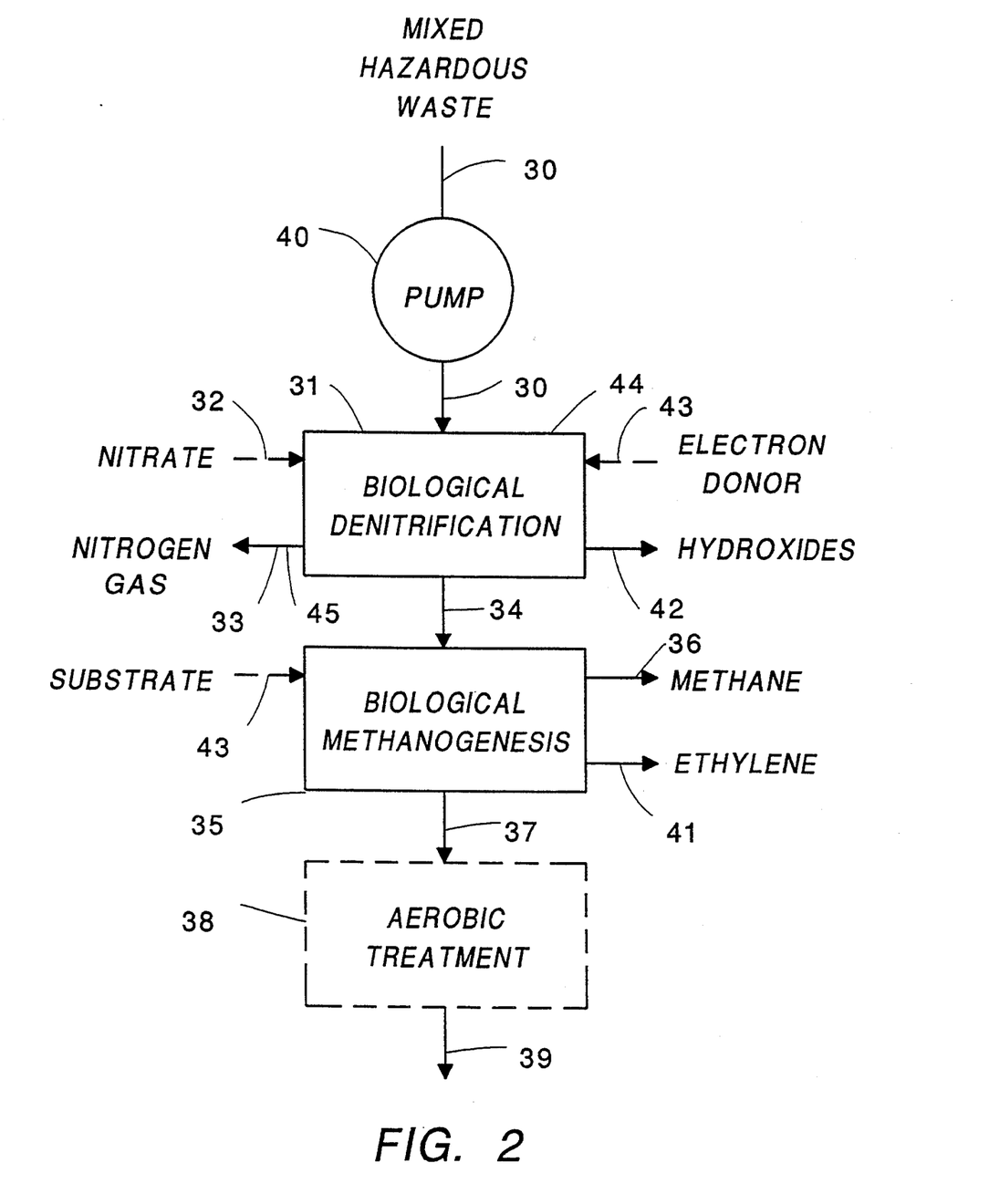
FIG. 2 is a schematic diagram of a second preferred embodiment of the invention.

Reference is now made to FIG. 2 which is a highly schematic block diagram illustrating a second preferred embodiment of the invention, the dashed lines representing possible variations in the process. Mixed hazardous waste 30 is input to the process by pump 40. Mixed hazardous waste may include aromatic hydrocarbons and/or halogenated hydrocarbons, heavy metals, acids and salts. Examples of aromatic hydrocarbons include benzene, toluene, ethylbenzene, xylenes, phenols and cresols. Examples of halogenated hydrocarbons include tetrachloroethylene (PCE), trichloroethylene (TCE), and 1,1,1-trichloroethane (TCA). Examples of heavy metals include copper, lead, zinc and mercury. Examples of acids include nitric acid, sulfuric acid and hydrochloric acid. Examples of salts include sodium nitrate, sodium sulfate and sodium chloride. The process involves an initial denitrifying step and a subsequent methanogenic step, without an intermediate sulfate-reduction step. A third, aerobic processing step may also be included.

Mixed hazardous waste 30 is delivered to first reactor 31 wherein the denitrification step occurs. The denitrification step is operated as explained above for the first preferred embodiment. With first (denitrification) reactor 31 operated as a "pH stat," the target pH would be chosen to optimize both the denitrification and the downstream methanogenesis process steps. For example, unless enrichment of alkaliphilic methanogens that prefer a pH of 8.1 to 9.2 is envisioned, a target pH of about 7.4 would be used.

If necessary, a supplemental electron acceptor, such as nitrate 32, and/or a supplemental electron donor 43, such as methanol, are added to first reactor 31. Metal hydroxides 42 and first liquid effluent 34 are removed from first reactor 31. Nitrogen gas 33 may be removed from first liquid effluent 34 using one of the methods described above. In one embodiment, first reactor 31 includes headspace 44 from which nitrogen gas 33 is removed by vacuum pump 45. Waste nitrogen gas 33 may be scrubbed to remove volatile hydrocarbons contained in it by contacting it with an aqueous waste stream, such as a portion of third liquid effluent 39, which portion is returned to first or second reactor 31 or 35 for further treatment.

First liquid effluent 34 is delivered to second reactor 35 wherein methanogenesis is accomplished. The methanogenic step is operated as noted above in the description of the first preferred embodiment. Dehalogenation and methanogenesis are accomplished, in part, by methanogenic bacteria of the species *Methanosarcina barkeri* and/or *Methanosarcina vacuolata*. The microorganisms are grown in either suspended culture or in biofilms and methane 36 and ethylene 41 are produced. Substrate 43, such as methanol, may be added to second reactor 35 to facilitate dechlorination of chlorinated hydrocarbons.

If residual organics concentrations are excessive, a final aerobic treatment step is incorporated into the process. In this case, second liquid effluent 37 is delivered to third reactor 38. Activated sludge and trickling filter unit processes are examples of appropriate aerobic process steps. After treatment, fourth liquid effluent 39 is removed from third reactor 38.

Figure 3:
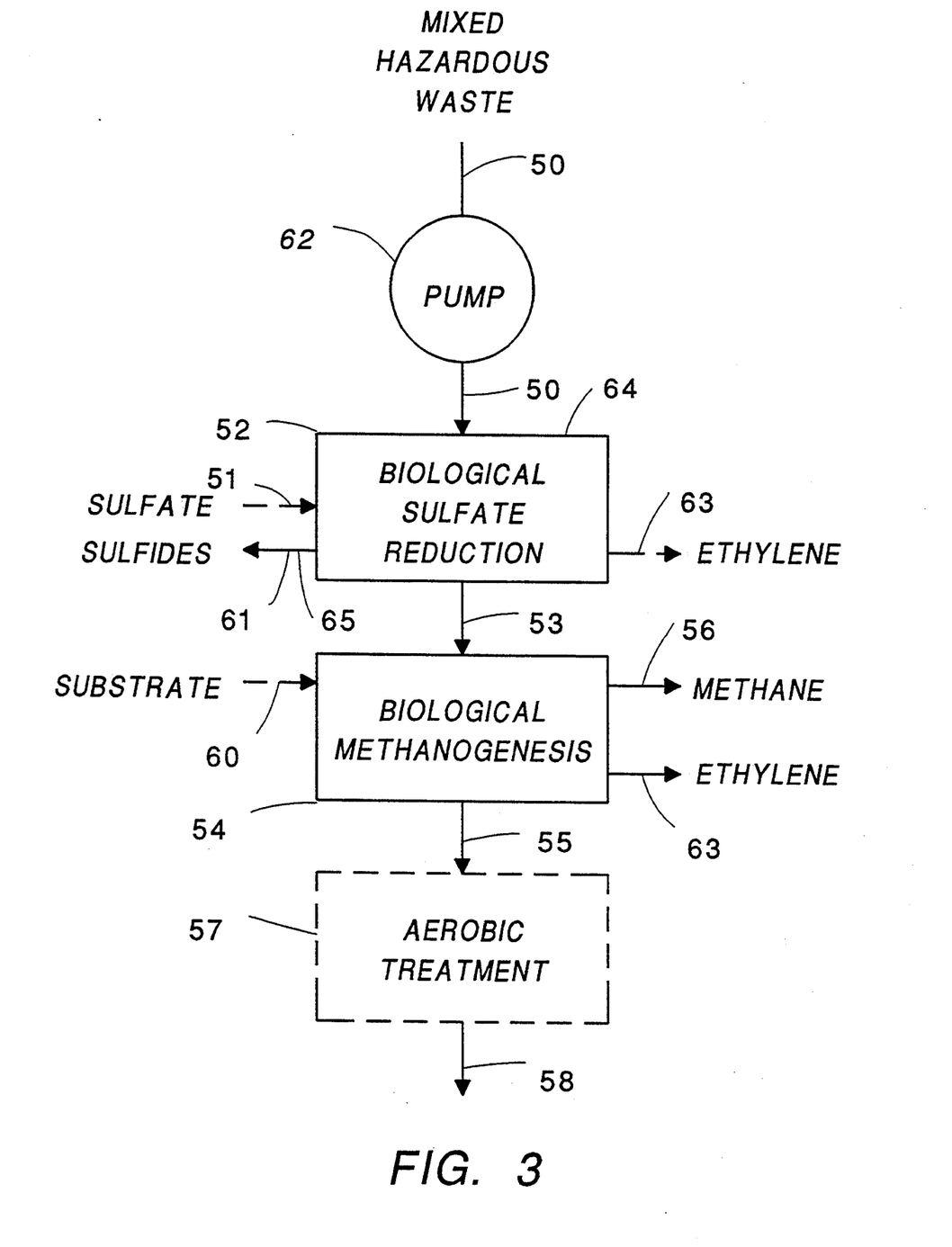
FIG. 3 is a schematic diagram of a third preferred embodiment of the invention.

Reference is now made to FIG. 3 which is a highly schematic block diagram illustrating a third preferred embodiment of the invention, the dashed lines representing possible variations in the process. Mixed hazardous waste 50 is input to the process by pump 62. The process involves an initial sulfate-reduction step and a subsequent methanogenic step. A third, aerobic processing step may also be included.

The initial sulfate-reduction step is accomplished in first reactor 52 which is operated as noted above for the first preferred embodiment. Additional information on process step options is provided in U.S. Pat. No. 5,076,927. Sulfate 51 may be added or it may be present in mixed hazardous waste 50. Hydrogen sulfide gas (e.g., sulfides 61) may be removed from first liquid effluent 53 using one of the methods described above. In one embodiment, first reactor 52 includes headspace 64 from which hydrogen sulfide gas 61 is removed by vacuum pump 65. Waste hydrogen sulfide gas 61 may be scrubbed to remove volatile hydrocarbons contained in it by contacting it with an aqueous waste stream, such as a portion of third liquid effluent 58, which portion is returned to first or second reactor 52 or 54 for further treatment. Biological dechlorination of PCE and TCE may produce ethylene 63.

First liquid effluent 53 of first reactor 52 is transferred to second reactor 54. In a second methanogenic step, dechlorination and methane 56 production occur. Dehalogenation and methanogenesis are accomplished, in part, by methanogenic bacteria of the species *Methanosarcina barkeri* and/or *Methanosarcina vacuolata*. Reductive PCE dechlorination by methanogens to produce ethylene 63 during metabolism of a primary substrate 60, such as acetate or methanol, has been documented. Therefore, one such substrate 60 is added to the reactor if one is not present in first liquid effluent 53 from the sulfate-reduction step. The specific microorganisms that would be enriched in reactors operated as indicated above would depend on the salinity and temperature of the reactor content. If second reactor 54 is operated at a relatively high pH (above pH 8), over 95 percent of the hydrogen sulfide gas is ionized. At pH 7, about two thirds is ionized. Ionized (soluble) sulfides 61 concentrations over 200 milligrams per liter (as sulfur) are toxic to methanogens.

If residual organics concentrations are excessive, a final aerobic treatment step can be incorporated into the process by transferring second liquid effluent 55 to third reactor 57. Activated sludge and trickling filter unit processes are examples of appropriate aerobic process steps for producing third liquid effluent 58.

Applicants have discovered a novel and unobvious new use for the processes claimed in the U.S. Pat. No. 5,076,927 of one of them. In the referenced patent, methods for culturing microorganisms, and, specifically, for culturing sulfate-reducing bacteria and methane-producing bacteria in at least two reactors in series, are disclosed. The invention in the referenced patent provides a method for neutralizing and removing metals and sulfate from acid mine drainage and other acidic metal sulfate solutions. Sulfate is used as the sole electron acceptor in the biological reduction process. The electron donors are volatile acids or their disassociation products, such as propionic acid, propionate ion, butyric acid, butyrate ion, lactic acid and lactate ion.

Applicants have discovered that the methods in the referenced patent can be used to biologically oxidize aromatic hydrocarbons as electron donors and to biologically reduce halogenated hydrocarbons as electron acceptors. The new use is illustrated in FIG. 3. Mixed hazardous waste 50 is the primary input to the process. The method accomplishes at least one function selected from the group consisting of biologically oxidizing aromatic hydrocarbons, and biologically reducing halogenated hydrocarbons, in at least two reactors in series.

A liquid substrate (i.e., mixed hazardous waste 50) comprising a dissolved sulfate 51 and more moles of at least one dissolved electron donor with a molecular weight greater than that of acetic acid (e.g., an aromatic hydrocarbon in mixed hazardous waste 50) than are required by sulfate-reducing bacteria to biologically reduce at least a portion of the dissolved sulfate, are delivered to first reactor 52. The substrate is fermented in first reactor 52 under anaerobic conditions at a pH between about 6 to 8, at a temperature between about 30 degrees C. to 40 degrees C. and at a mean cell residence time less than that required for essentially complete oxidation of acetic acid by sulfate-reducing bacteria at the selected pH and temperature to produce sulfides 61 and first liquid effluent 53. The concentration of the sulfides 61 generated by the fermentation process in the liquid in first reactor 52 is reduced by conventional means 65.

First liquid effluent 53 from first reactor 52 is delivered to second reactor 54. First liquid effluent 53 is fermented in second reactor 54 at a pH of between about 6.8 to 7.4, at a temperature between about 20 degrees to 65 degrees C. and at a mean cell residence time greater than the mean cell residence time required for essentially complete utilization of acetic acid by methane-producing bacteria to produce methane and second liquid effluent 55. Reductive dehalogenation (e.g., dechlorination) occurs in first reactor 52 and in second reactor 54. Dehalogenation and methanogenesis are accomplished, in part, by methanogenic bacteria of the species *Methanosarcina barkeri* and/or *Methanosarcina vacuolata*.

Methane 56, ethylene 63 and second liquid effluent 55 are removed from second reactor 54. If necessary, second liquid effluent 55 is delivered to third reactor 57 for aerobic treatment. After aerobic treatment is completed, third liquid effluent 58 is removed from third reactor 57.

EXAMPLE

In general, the serum bottle modification of the Hungate technique was used. The mineral portion of the medium was mixed in a six-liter boiling flask. Chemicals of the mineral solution portions were added to four liters of distilled water and heated to boiling. The medium was then cooled to 40° C. while being gassed with oxygen-free nitrogen. HCl was added to the methanogen media to adjust the pH between 6.8–7.2. The pH was measured using a Markson microcomputer-based pH/ORP controller, as was temperature and oxidation reduction potential (ORP). One hundred and forty milliliters (ml) of the mineral solution was then transferred to serum bottles. These bottles are sold having a 125 ml capacity but actually have a 160 ml capacity. Each bottle was sealed with a grey Teflon ®-faced butyl rubber stopper.

To the serum bottles were added the trace element solution, vitamin solution and reductant solution from stock solutions. All were added using 20 gauge needles and were filter sterilized using 0.2 micron sterile filters. Filtered xenobiotic compounds were then added using a syringe. The aromatic compounds were added in an undiluted form. The chlorinated hydrocarbons were diluted by 1:10,000 in deoxygenated water in sealed serum bottles and then added. Finally, bacteria were added, 2 ml to each bottle, from previously growing stock solutions.

Each xenobiotic concentration was tested in triplicate. In addition, abiotic controls were run for each xenobiotic compound in triplicate. All bottles were incubated for two months in the dark at 37° C.

Prereduced enriched methanogenic medium (PREM medium) was used. To the mineral solution described in Table 1 were added 1 ml/1000 ml of the trace element solution of Table 2, 1 ml/1000 ml of the vitamin solution in Table 3 and 5 ml/1000 ml of the reductant solution of Table 4.

Methanol was used as the electron donor in the methanogen dechlorination experiments at a concentration of 50 mg/l. Approximately 1 mg/l of chlorinated hydrocarbons was also used.

Results were generated by analyzing aliquots of controls and samples by gas chromatography/mass spectrometry in accordance with EPA Method 8240. The analyses were conducted by Inter-Mountain Laboratories, Inc., a Bozeman, Montana, laboratory that has been certified by EPA Region VIII and routinely participates in EPA Water Study and Water Pollution performance series audits.

The results of methanogen screening for the ability to cometabolize chlorinated hydrocarbons are presented in Table 5. Only the controls and bottles with visual evidence of growth (stopper bulging out due to gas formation and/or a significant decrease in the clarity of the medium) were analyzed. Of course, lack of visual evidence of growth does not mean that growth or the biotransformations sought did not occur. Moreover, growth of anaerobic bacteria can be prevented or reduced by a variety of factors, some of which are not amenable to visual verification.

The chlorinated hydrocarbons were more volatile with the following expected ratios of the concentration in the headspace to the concentration in the liquid medium: PCE—0.93, TCE—0.50 and TCA—1.1. Partition occurred in both the stock solution bottles and in the test bottles. Thus, partitioning should have reduced the methanogen control liquid concentrations of PCE, TCE and TCA to about 0.8 mg/l.

TABLE 1

| Mineral Solutionn Used in Preparation of Methanogen Medium | |
|---|---|
| Constituent | Concentration, mg/l |
| Ammonium bicarbonate, $NH_4HCO_3$ | 3,000 |
| Ammonium chloride, $NH_4Cl$ | 180 |
| Calcium chloride, $CaCl_2.2H_2O$ | 120 |
| Magnesium chloride, $MgCl_2.6H_2O$ | 170 |
| Potassium phosphate, dibasic, $K_2HPO_4$ | 450 |
| Potassium phosphate, monobasic, $KH_2PO_4$ | 450 |
| Sodium chloride, NaCl | 900 |
| Yeast extract | 1,000 |

TABLE 2

| Trace Element Solution Used in Preparation of Methanogenic Medium | |
|---|---|
| Constituent[a] | Concentration, mg/l |
| Boric acid, $H_3BO_3$ | 100 |
| Cobalt chloride, $CoCl_2.6H_2O$ | 1,000 |
| Copper chloride, $CuCl_2.2H_2O$ | 80 |
| Ferric chloride, $FeCl_3.6H_2O$ | 20,000 |
| Manganese chloride, $MnCl_2.4H_2O$ | 6,000 |
| Sodium molybdnate, $Na_2MoO_4.2H_2O$ | 100 |
| Zinc chloride, $ZnCl_2$ | 80 |

[a]One ml added to 1,000 ml of mineral solution.

TABLE 3

| Vitamin Solution Used in Preparation of Methanogenic Medium | |
|---|---|
| Constituent[a] | Concentration, mg/l |
| para-Aminobenzoic acid | 50 |
| Biotin | 50 |
| Cobalamin | 5 |
| Folic acid | 20 |
| Nicotinic acid | 50 |
| Pyridoxine hydrochloride | 100 |
| Riboflavin | 50 |
| Thiamine hydrochloride | 50 |

[a]One ml added to 1,000 ml of mineral solution.

TABLE 4

| Reductant Solution Used in Preparation of Methanogenic Medium | |
|---|---|
| Constituent[a] | Concentration, mg/l |
| Resazurin | 300 |
| Sodium dithionite, $Na_2S_2O_4$ | 1,000 |
| Sodium sulfide, $Na_2S.9H_2O$ | 12,000 |

[a]Five ml added to 1,000 of mineral solution.

A significant amount of abiotic removal of chlorinated hydrocarbons occurred. The results indicate unequivacably, however, that statistically significant reductions of chlorinated hydrocarbons, in some cases to below the limit of detection of the method (0.005 mg/l), occurred. Those reductions that are statistically significant when compared to the abiotic controls are underlined in Table 5.

TABLE 5

| Results of Microorganism Screening with Chlorinated Hydrocarbons | | | |
|---|---|---|---|
| | Average concentration, mg/l | | |
| Medium/microorganism | PCE | TCE | TCA |
| Methanogen-methanol | | | |
| Control | 0.14 | 0.28 | 0.22 |
| Methanosarcina barkeri | 0.045 | — | <0.005 |
| Methanosarcina vacuolata | <0.005 | — | — |

The following methanogens are capable of dechlorinating the indicated compounds:

Methanosarcina barkeri—TCA

Methanosarcina vacuolata—PCE

Methanosarcina barkeri is also able to cometabolize PCE in that it reduced the concentration of PCE of about 70 percent in a single analyzed sample and produced some TCE (<0.05 mg/l).

A component scan of the contents of one of the bottles in which Methanosarcina vacuolata cometabolized PCE revealed the presence of cis 1,2-dichloroethylene (0.18 mg/l). A component scan of another bottle originally containing PCE and Methanosarcina vacuolata revealed the presence of <0.005 mg/l of TCE. Freedman and Gossett in Applied Environmental Microbiology, Vol. 55, pp. 2144–2151 (1989) have reported the transformation of PCE (via TCE) to 1,2-dichloroethylenes under methanogenic conditions. As was noted above, Fathepure and Boyd in Applied and Environmental Microbiology, Vol 54, pp. 2976–2980 (1988) documented the transformation of PCE to TCE by axenic cultures of other Methanosarcina species (Methanosarcina mazei strain S6 and Methanosarcina sp. strain DCM) grown on methanol. They did not report further degradation of TCE to 1,2-dichloroethylenes by their axenic cultures.

A component scan of the contents of one of the bottles in which *Methanosarcina barkeri* cometabolized TCA revealed the presence of 1,1-dichloroethane (0.27 mg/l). This compound has been found to be formed in sediment and bacterial culture microcosms that were spiked with TCA. Others have reported that 1,1-dichloroethane was produced by heterotrophic growth of Desulfobacterium autotrophicum in a lactate medium containing TCA and by autotrophic growth of *Methanobacterium thermautotrophicum* in a medium containing TCA. Transformation of TCA to 1,1,-dichloroethane (which was not degraded further) by all cell suspensions of *Autotrophicum woodii*, has been documented.

Many variations of the invention will occur to those skilled in the art. All such variations within the scope of the claims are intended to be within the scope and spirit of the invention.

We claim:

1. A process for the microbial dehalogenation of tetrachloroethylene and trichloroethylene comprising at least one of said compounds to a microorganism capable of dehalogenating both tetrachloroethylene and trichloroethylene wherein the microorganism is selected from the group consisting of *Methanosarcina barkeri* ATCC 43241, *Methanosarcina vacuolata* ATCC 35090, and mutants thereof.

2. The process of claim 1 wherein the microorganism is *Methanosarcina barkeri* ATCC 43241.

3. The process of claim 1 wherein the microorganism is *Methanosarcina vacuolata* ATCC 35090.

4. The process of claim 1 wherein the microorganism is a mutant of either *Methanosarcina barkeri* ATCC 43241 or *Methanosarcina vacuolata* ATCC 35090.

* * * * *

UNITED STATES PATENT AND TRADEMARK OFFICE
CERTIFICATE OF CORRECTION

PATENT NO. : 5,342,769
DATED : August 30, 1994
INVENTOR(S) : Robert M. Hunter and Frank M. Stewart It is certified that error appears in the above-identified patent and that said Letters Patent is hereby corrected as shown below:

Column 1,
Before line 5, add the following paragraph:

-- The present application is a continuation-in-part of application Ser. No. 07/926,047 filed August 4, 1992, and entitled Method and Apparatus for Bioremediation of Mixed Hazardous Wastes, now Patent No. 5,922,204. --

Column 3,
Line 54, cancel "acetate Cells" and insert -- acetate. Cells --.

Column 12,
Line 48, cancel "PCE of" and insert -- PCE by --.

Column 14,
Line 4, cancel beginning with "1. A process for" to and including "mutants thereof."
Line 11, insert the following claim:

--1. A process for the microbial dehalogenation of tetrachloroethylene and trichloroethylene comprising exposing at least one of said compounds to a microorganisim capable of dehalogenating both tetrachloroethylene and trichloroethylene wherein the microrganism is selected from the group consisting of *Methanosarcina barkeri* ATCC 43241, *Methanosarcina vacuolata* ATCC 35090, and mutants thereof. --

Signed and Sealed this

Twenty-fifth Day of December, 2001

*Attest:*

*Attesting Officer*

JAMES E. ROGAN
*Director of the United States Patent and Trademark Office*